United States Patent [19]
Mattox

[11] Patent Number: 4,906,274
[45] Date of Patent: Mar. 6, 1990

[54] ORGANIC STABILIZERS

[75] Inventor: John R. Mattox, Perkasie, Pa.

[73] Assignee: Rohm and Haas Company, Philadelphia, Pa.

[21] Appl. No.: 118,366

[22] Filed: Nov. 6, 1987

[51] Int. Cl.$^4$ ................... A01N 43/78; C07D 275/02
[52] U.S. Cl. ........................................... 71/67; 71/90; 71/124; 514/373; 548/213
[58] Field of Search ............................ 71/90, 124, 67; 548/213

[56] References Cited
PUBLICATIONS

Shima et al., Chem. Abst., vol. 82 (1975), 31888t.

*Primary Examiner*—Glennon H. Hollrah
*Assistant Examiner*—Susan P. Treanor
*Attorney, Agent, or Firm*—Michael B. Fein; Terence P. Strobaugh

[57] ABSTRACT

Organic stabilizers are used to stabilize various materials which are normally unstable neat or in solution. These compositions exhibit bactericidal, fungicidal and algaecidal properties.

11 Claims, No Drawings

ORGANIC STABILIZERS

This invention relates to stable compositions of 3-isothiazolones, their preparation, and their use in controlling living organisms. The isothiazolones which are stabilized include those disclosed in U.S. Pat. Nos. 3,523,121 and 3,761,488 as represented by the following structural formula

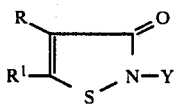

I wherein

Y is an unsubstituted or substituted alkyl of from 1 to 18 carbon atoms, an unsubstituted or halo substituted alkenyl or alkynyl of from 2 to 8 carbon atoms, and, preferably, from 2 to 4 carbon atoms, an unsubstituted or substituted cycloalkyl of from 5 to 8 carbon atoms, an unsubstituted or substituted aralkyl or an unsubstituted or substituted aryl;

R is hydrogen, halo, or a $(C_1-C_4)$alkyl and $R^1$ is hydrogen, halo or $(C_1-C_4)$alkyl.

Representative Y substituents include methyl, ethyl, propyl, isopropyl, butyl, hexyl, octyl, cyclohexyl, benzyl, 3,4-dichlorobenzyl, 4-methoxybenzyl, 4-chlorobenzyl, 3,4-dichlorophenyl, 4-methoxyphenyl, hydroxymethyl, chloromethyl, chloropropyl and the like.

Preferred isothiazolones are 5-chloro-2-methyl-3-isothiazolone, 2-methyl-3-isothiazolone, 2-octyl-3-isothiazolone, 4,5-dichloro-2-cyclohexyl-3-isothiazolone and 4,5-dichloro-2-octyl-3-isothiazolone.

Japanese Pat. No. 12243183 discloses stabilizing a mixture of an isothiazolone and 2-hydroxymethyl-2-nitro-1,3-propanediol with a diol solvent. However, 2-hydroxymethyl-2-nitro-1,3-propanediol is a formaldehyde releaser, which is known to stabilize isothiazolones (see U.S. Pat. Nos. 4,165,318 and 4,129,448).

European Patent Application 194,146 discloses stabilizing isothiazolones in non-aqueous, salt-free systems by several hydroxylic solvents, outstanding among them dipropylene glycol.

Thus, until now means for stabilization of isothiazolones against thermal degradation or storage degradation has generally been by metal salts, formaldehyde or formaldehyde releasers.

Both formaldehyde or formaldehyde-releasers and salt stabilization of isothiazolones have some drawbacks. Formaldehyde is a suspected carcinogen, and it is desirable not to use formaldehyde in applications where contact with human skin or lungs may occur.

This invention is directed to stable biocidal isothiazolone compositions in which (1) water is substantially eliminated, (2) salt neutralization is eliminated and (3) the need for nitrate stabilizer salts is substantially eliminated.

The orthoesters of this invention (II, infra) are those having the following general formula:

$$CX(OR^2)(OR^3)(OR^4)$$  II wherein

X is hydrogen, alkyl, for example alkyl of from 1 to 18 carbon atoms, or a substituted oxy of the formula $OR^2$ wherein $R^2$ is as defined below, or aryl, for example, mononuclear aryl such as phenyl and the like.

$R^2$, $R^3$ and $R^4$ are the same or different radical selected from alkyl, for example, alkyl of from 1 to 18 carbon atoms such as methyl, ethyl, propyl, butyl, octyl and the like, and, preferably, lower $(C_1-C_5)$alkyl, cycloalkyl, for example, cycloalkyl of from 3 to 7 nuclear carbon atoms such as cyclopropyl, cyclobutyl, cyclopentyl, cyclohexyl, cycloheptyl and the like, aryl, for example, mononuclear aryl of from 6 to 10 carbon atoms such as phenyl and the like, alkylaryl, for example lower alkyl $(C_1-C_6)$ substituted mononuclear aryl such as methylphenyl, dimethylphenyl and the like; or arylalkyl for example, mononuclear arylalkyl such as benzyl, phenethyl and the like.

The preferred orthoesters of this invention are those wherein $R^2$, $R^3$ and $R^4$ are all lower $(C_1-C_5)$alkyl and X is hydrogen, lower $(C_1-C_5)$alkyl or aryl. Especially preferred are trimethyl orthoformate, triethyl orthoformate, triethyl orthoacetate, trimethyl orthovalerate, and trimethyl orthobenzoate.

This invention comprises a composition which contains from about 0.1 to about 99.9 parts of one or more isothiazolones and an effective amount of an orthoester of Formula II (supra), preferably, an orthoester in the range of from 0.1 to about 99.9 percent.

More preferably, the composition comprises at least one isothiazolone wherein Y is $C_1-C_{18}$alkyl or $C_3-C_{12}$cycloalkyl; R is hydrogen or halo; and $R^1$ is hydrogen or halo. Typical formulation ranges are illustrated in the following Table (all percentages are parts by weight) for both a concentrated solution of the isothiazolone and a dilute solution. For certain uses, such as shipping of large quantities, more concentrated solutions may also be utilized.

| FORMULATIONS TABLE | | |
| --- | --- | --- |
| Isothiazolone (I, Supra) | ORTHOESTER (II, supra) | Solvent |
| 0.1-99.9% | 0.1%-99.9% Preferred | 0-99.8% |
| 1-50% | 1-25% More Preferred | 25-98% |
| 1-25% | 1-10% | 65-98% |

When it is desired to package the isothiazolone with only the stabilizer and no other organic solvent or water present the amount of stabilizer or mixture of stabilizers employed will be from about 1 percent to about 25 percent. The isothiazolone may be present in a bulk form or packaged or encapsulated in some manner, including a form for controlled release. The ratio of orthoester to isothiazolone is preferably from about 1:7 to about 1.5:1.

Solvents other than orthoesters may be used to dissolve the isothiazolones and may be any organic solvent which dissolves the isothiazolones, are compatable with the proposed end use, do not destabilize the isothiazolone, and do not react with the orthoester to eliminate its stabilizing action.

Hydroxylic solvents, for example, polyols, such as glycols, alcohols and the like, may be used. Under conditions of high dilution and high ratios of stabilizer to isothiazolone, glycols may be successfully used.

Preferred solvents are capped polyols, wherein the free hydroxy is replaced with an ether or ester function.

Especially preferred are 2,5,8,11-tetraoxadecane, commonly known as triethylene glycol dimethyl ether, and 4,7-dioxaundecanol-1 acetate, commonly known as diethylene glycol butyl ether acetate.

The amounts of orthoester employed will vary depending on use conditions and concentrations of the isothiazolone in the mixture. In more concentrated solutions, effective amounts of orthoester based on isothiazolone are in the ratios of from about 1:4 to about 1:2. Obviously higher amounts may be used, but at additional cost. At low levels of dilution of the isothiazolone (such as from 1 to 2 percent isothiazolone in the solvent), the ratio of stabilizer to isothiazolone can range from about 1:7 to about 2:1.

This invention permits the stabilization of isothiazolones wherein the previously necessary stabilization salts are substantially reduced and even eliminated. Useful stabilization salts which can be employed are those disclosed in U.S. Pat. Nos. 3,870,795 and 4,067,878 and include stabilization salts selected from:

(1) Metal nitrates, where the metal is barium, cadmium, calcium, chromium, cobalt, copper, iron, lead, lithium, magnesium, manganese, mercury, nickel, sodium, silver, strontium, tin, zinc and the like; and (2) Copper (2+) salts where the anion is halide, sulfate, nitrate, nitrite, acetate, chlorate, perchlorate, bisulfate, bicarbonate, oxalate, maleate, carbonate, or phosphate and the like.

Uses of these new organically stabilized biocides are typically at any locus subject to contamination by bacteria, fungi or algae. Typically loci are in aqueous systems such as water cooling, laundry wash water, oil systems such as cutting oils, oil fields and the like where microorganisms need to be killed or where their growth needs to be controlled.

The stabilized biocide compositions of this invention are advantageous over salt stabilized isothiazolones described in the art and are the biocides of choice where salts pose a problem. For example, certain emulsions upon the addition of a salt may coagulate. The compositions of this invention avoid this problem and therefore can be used in emulsions such as photographic emulsions, coating emulsions, (e.g. paints) to form solid protective or decorative films; electronic circuitry, wood, metals, plastics, fibers, membranes, carpet backings, ceramics and the like where surfaces need to be coated or protected, adhesives, caulks, and sensitive emulsions.

In many salt stabilized biocide systems of the prior art there is a potential for solids formation caused by interactions with other salts in the system, interaction with certain salt forming organics, by the conversion to organic salts, or simply by incompatibility with the system. The stabilized biocide compositions of this invention would be preferred in those systems. Also, the compositions of this invention are useful in fuel systems such as diesel fuel, gasoline, kerosene, certain alcohols, and the like, because they eliminate the possibility of salt deposits on component parts. Another reason for eliminating salts is to avoid an environment in which corrosion can occur. For example, chloride salts (among others) have a corrosive effect on many metals and are to be avoided where possible. In water treatment systems where low cation and anion levels are important, this is especially true. Those familiar with the art in various areas where biological growth needs to be controlled will quickly recognize those applications where significant reduction of or elimination of salts will be desired. In many cases it is necessary to eliminate interactions between the stabilizing salts and other components of the system or formulation components which otherwise could reduce the performance or value of such systems.

It is also recognized that the isothiazolone stabilizers of this invention have other applications known to those skilled in the art. For example, orthoformates are known to serve as reactive scavengers for molecules containing —OH, —NH$_2$, —SH and other nucleophilic groups. A biocide formulation stabilized with an orthoformate would be particularly advantageous where the dual function of biocidal/biostatic activity and scavenging would lead to advantageous results.

Because isothiazolone biocides are so active, the low level required to achieve stabilization also makes them ideal when compared to many known biocides because at the low levels required they are not likely to interfere with other components in systems requiring protection or with systems upon which the protected systems will be applied.

Potential areas of general application include disinfectants, sanitizers, cleaners, deodorizers, liquid and powder soaps, skin removers, oil and grease removers, food processing chemicals, dairy chemicals, food preservatives, animal food preservatives, wood preservation, paint, lazures, stains, mildewcides, hospital and medical antiseptics, metal working fluids, cooling water, air washers, petroleum production, paper treatment, paper mill slimicides, petroleum products, adhesives, textiles, pigment slurries, latexes, leather and hide treatment, petroleum fuel, laundry sanitizers, agricultural formulations, inks, mining, nonwoven fabrics, petroleum storage, rubber, sugar processing, tobacco, swimming pools, cosmetics, toiletries, pharmaceuticals, chemical toilets, household laundry products, diesel fuel additives, waxes and polishes and many other applications where water and organic materials come in contact under conditions which allow the growth of undesired microorganisms.

In the stabilization of plastic articles, it is desirable to eliminate salts in the isothiazolones, as salts may contribute to deterioration of optical properties and/or increase water pickup and haze levels.

In some cosmetic formulations, it is also important to have low water and salt content. Eliminating nitrate salts avoids the possibility of nitrosamine formation with any amines present in the formulation. Removal of multivalent cations from the biocide may also eliminate the known possibility of creating physical incompatibility problems in certain cosmetic formulations caused by precipitation of salts or complexes.

It is known in the art that the performance of biocides can frequently be enhanced by combination with one or more other biocides. In fact, there have been numerous examples of synergistic combinations of biocides. Thus, other known biocides may be combined advantageously with the stabilized isothiazolones of this invention.

Isothiazolones are used as disinfectants, in oil field water treatment, as watercooling system microbiocides, as preservatives for aqueous dispersions or organic polymers, as wood pulp white water slimicides, as cosmetic preservatives, as cutting oil, jet fuel, and heating oil preservatives, and the like. Solutions of isothiazolones are also applied to a solid substrate, such as fabric, leather, or wood, as a preservative, or admixed with plastics.

The products of this invention are especially useful as preservatives for the following:

1. Cosmetics, as it eliminates or substantially reduces the presence of nitrates which under certain conditions in the presence of amines or amine precursors may lead to the formation of nitrosoamines.

2. Oils and fuels, since added salts and moisture are eliminated or minimized thus preventing potential corrosion, deposition or sludge formation.

3. Emulsions and dispersions that are sensitive to divalent cations are those contained in a wide variety of products, such as paints, cosmetics, floor polishes and binders 4. Plastics, as it eliminates or substantially reduces precipitated salts which can contribute directly or indirectly to haze, opacity, or physical weakness in the surface.

The term "orthoester" is well-known in the field of organic chemistry. They can also be named as ethers. Thus triethyl orthoacetate is named 1,1,1-trimethoxyethane, trimethyl orthobenzoate is tris(methoxy)methylbenzene.

The orthoesters (1A) of this invention are known compounds or may be prepared by methods well known to those skilled in the art. Thus symmetrical ($R^2=R^3=R^4$) orthoesters may be made by reacting a 1,1,1-trihalo compound with an appropriately substituted sodium oxide as illustrated by the following equations:

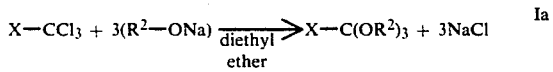

Ia

Orthocarbonate esters may be prepared by a related method

Ib

Mixed orthoesters, ($R^2 \neq R^3$), may be prepared from the iminoether hydrochloride of the parent acid as illustrated by the following equations:

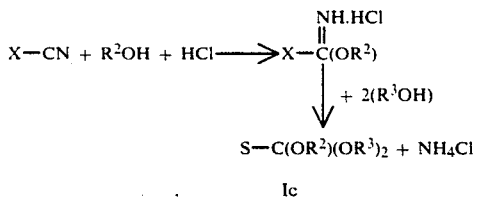

Ic

Derivatives of benzoic acid and related aromatic acids may be prepared by similar chemistry or by a controlled Grignard reaction on an orthocarbonate.

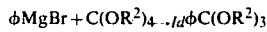

The following examples will further illustrate this invention, but are not intended to limit it in any way. All parts and percentages are by weight and all temperatures in degrees Centigrade, unless otherwise stated.

For comparison of the stabilization of the compositions of this invention with known materials the following tests were employed using a thermally-controlled solid metal block with bored holes as receptacles for the vials and with demonstrated temperature control, vials of stabilizer, solvent, and isothiazolone were made up and heated for fixed periods of time. The percentage of the starting isothiazolone remaining was determined by high performance liquid chromatography (HPLC). Temperatures of 40°, 55°, and 70° C. were used. Results were considered indicative of acceptable stability when remainder values indicated essentially no loss during the time specified for the isothiazolone or isothiazolone mixture studied.

I. Stability Test for 5-Chloro-2-methylisothiazolin-3-one/2-Methylisothiazolin-3-one The 3:1 mixture of 5-chloro-2-methylisothiazolin-3-one/2-methylisothiazolin-3-one (16.2%) is mixed at 14% active ingredient (AI) in triglyme (76.8%) with the chosen stabilizer (7%). The retention of AI is measured after four weeks at 40° C. and after one and two weeks at 70° C. HPLC is used to measure of AI. Maintenance of AI must be >85% to meet the target of most preferred. Other stabilizers may be less effective in the test, but may be adequate for stabilization under shorter time, less exacerbated conditions. This is compared with a 3:1 mixture of 5-cloro-2-methylisothiazolin-3-one/2-methylisothiazolin-3-one stabilized with magnesium nitrate (15%).

The following results were obtained

| Ex. No. | Stabilizer | 1 week, 70° | 2 weeks, 70° | 4 weeks, 40° |
|---|---|---|---|---|
| 1 | None | F | F | 32 |
| 2 | Mg(NO3)2, 15% | P | P | P |
| 3 | Trimethyl orthoformate (TOF) | P | P | P |
| 4 | Triethyl orthoformate (TEOF) | P | P | P |
| 5 | Triethyl orthoacetate (TOA) | P | P | P |
| 6 | Triethyl orthovalerate (TOV) | P | P | P |
| 7 | Tetramethyl orthocarbonate (TOC) | P | P | P |
| 8 | Trimethyl orthobenzoate (TOB) | P | P | P |

(P indicates greater than 85% retention of AI. F indicates less than 10% retention, ie. complete and unacceptable loss of activity.)

II. Ratios of Stabilizer to Isothiazolone

Data are here presented for weeks of stability at 55°. In all cases, AI was 14% of the mixed isothiazolone, the stabilizer was at percentages of from 0 to 7, and the remainder was the solvent. BCA=4,7-dioxaundecanol-1-acetate; DPG=dipropylene glycol; TEOF=triethyl orthoformate; P and F are as defined earlier. (Some stability is offered by certain solvents in the absence of stabilizer, but not of commercially-acceptable magnitude.)

| | Ratio of Stabilizer to Isothiazolone at 14% AI | | | | |
|---|---|---|---|---|---|
| Ex. | | | | % AI Remaining After 55° C. | |
| No. | Stabilizer, % | Solvent | 2 weeks | 4 weeks | 8 weeks |
| 9 | TEOF | 7 | BCA | P | P | P |
| 10 | TEOF | 5 | BCA | P | P | P |
| 11 | TEOF | 3 | BCA | P | P | 50 |
| 12 | TEOF | 1 | BCA | 50 | 15 | F |
| 13 | None | | BCA | 55 | 40 | 15 |
| 14 | TEOF | 7 | DPG | P | P | P |
| 15 | TEOF | 5 | DPG | P | P | P |
| 16 | TEOF | 3 | DPG | P | F | F |
| 17 | TEOF | 1 | DPG | F | F | F |
| 18 | None | | DPG | F | F | F |

| | Ratios of Stabilizer to Isothiazolone at 1.5% AI | | | | |
|---|---|---|---|---|---|
| Ex. | | | | % AI Remaining After 55° C. | |
| No. | Stabilizer, % | Solvent | 2 weeks | 4 weeks | 8 weeks |
| 19 | TEOF | 2 | BCA | P | P | P |

| | | | | | |
|---|---|---|---|---|---|
| 20 | TEOF | 1 | BCA | P | P | P |
| 21 | TEOF | 0.5 | BCA | P | P | P |
| 22 | TEOF | 0.25 | BCA | P | P | P |
| 23 | None | | BCA | P | P | 80 |
| 24 | TEOF | 2 | DPG | P | P | P |
| 25 | TEOF | 1 | DPG | 30 | F | — |
| 26 | TEOF | 0.5 | DPG | F | F | — |
| 27 | TEOF | 0.25 | DPG | F | F | — |
| 28 | None | | DPG | F | F | F |

EXAMPLE 29

The neat isothiazolone (Structure I $R^1=Cl$, $R=H$, $Y=CH_3$; $R=R^1=H$, $Y=CH_3$ (3:1)) was stabilized with 5% or 20% triethyl orthoformate. These were stored one week at 40° and 55° and compared with unstabilized neat isothiazolone. The retention of active ingredient is shown below.

| | | % AI Remaining After Storage for 1 week at | |
|---|---|---|---|
| Stabilizer | % | 40° | 55° |
| None | — | 98.4 | 49.7 |
| TEOF | 5 | 100.0 | 99.7 |
| TEOF | 20 | 100.0 | 99.7 |

EXAMPLE 30

Hair Shampoo

A solution containing 1.5% of N-methyl-5-chloroisothiazolin-3-one and N-methylisothiazolin-3-one, and 2.0% of triethyl orthoformate as stabilizer in 96.5 dipropylene glycol is used as a preservative for a hair shampoo.

EXAMPLE 31

Shown below is percent of 5-chloro-2-methyl isothiazolin-3-one stabilized with trimethyl orthoformate in various solvents remaining after 2 weeks at 70° C., where initial isothiazolone content was 14% and 7% stabilizer is used, the balance being the solvents listed.

| Tetra-Glyme | Dipropylene Glycol | Propylene Glycol Methyl Ether Acetate | Diethylene Glycol Butyl Ether Acetate | Triacetin (glyceryl triacetate) | Ethylene Glycol Diacetate | DPG + 5% Water |
|---|---|---|---|---|---|---|
| 100 | 94 | 100 | 99 | 97 | 97 | 0 |

EXAMPLE 32

The advantage of eliminating salt shock in polymer emulsions is shown in the following example. Salt shock is observed as a precipitate or gelatinous mass that forms in the polymer emulsion when isothiazolone, containing stabilizers composed of divalent metal ions (e.g. $Mg^{++}$, $Cu^{++}$), is added as a preservative.

The polymer emulsion is initially passed through a 325 mesh screen to remove any gel that might be present from manufacture. Isothiazolone is added to a total amount of 30 ppm AI based on total polymer emulsion A 250 g. emulsion sample in a pint container is used. The sample is gently swirled after pipetting the appropriate amount of isothiazolone. The sample is inverted twice to mix and allowed to stand at ambient temperature for sixty minutes. The sample is again passed through a 325 mesh screen Any gel or precipitate on the screen is washed with deionized water to remove residual, uncoagulated polymer emulsion. The material remaining on the screen is collected and dried overnight at 50° C. This is followed by heating 1 hour at 150° C. to remove any remaining water. The residue is then weighed.

| | Gel Formation in Some Polymer Emulsions | | |
|---|---|---|---|
| | Isothiazolone | Stabilizer | Weight Gel Recovered mg/Kg emulsion |
| Emulsion 1 | 1.5% AI | magnesium nitrate copper nitrate | 2800, 2620 |
| | 1.5% AI | TEOF | 16 |
| Emulsion 2 | 1.5% AI | magnesium nitrate copper nitrate | 2520, 2424 |
| | 1.5% AI | TEOF | 51 |

The small amount of gel formed when the emulsion is preserved with stabilized isothiazolone (<60 mg/kg emulsion) will not be detrimental in the use of the emulsion in various applications such as paints, caulks, and the like. The amount of gel formed (>2400 mg/kg emulsion) when salt stabilized isothiazolone is used as a preservative would be easily visible and objectionable.

EXAMPLE 33

The following test was carried out to determine the microbial speed of kill of the orthoformate stabilized isothiazolone compared to the nitrate stabilized isothiazolone. This illustrated equivalent bactericidal activity when either the nitrate or orthoester stabilizer is used.

A. Description of the Speed of Kill Test

This test measures bactericidal activity in water free of organic matter It measures the loss of cell viability in an aqueous suspension of bacterial cells as a function of time when these cells are contacted with a defined concentration of test compound in the water. This is done by taking aliquots of the cell suspensions at the appropriate time interval and assaying the number of viable cells per milliliter by plate count or most probably number (MPN) methodology. These measurements are done on the cell suspensions containing no test compound. The viable cell counts of the test and control samples are then compared to determine cell death.

The inoculum is prepared by growing the bacteria on a slant for 24 hours and then harvesting the cells into phosphate buffer. To start the test at zero time, one volume of bacterial inoculum is added to 100 volumes of test solution containing compound at the final test concentration.

At appropriate time intervals, such as 2, 4 and/or 24 hours, aliquots of all the test samples and controls are assayed for viable cell count, reported as most probable number (MPN) per ml.

The results are calculated in terms of log10 reduction in MPN/ml compared to aqueous control This is done by taking the logarithm base 10 of the MPN/ml for the test count and subtracting this number from the logarithm base 10 of the MPN/ml for the aqueous control count. One log reduction corresponds to 90% kill, 2 logs reduction corresponds to 99% kill, 3 logs reduction corresponds to 99.9% kill, etc.

first vessel is transferred to the second vessel. After being mixed, one-half the resulting volume is removed from the second vessel and transferred to the third vessel. The entire cycle is repeated 8 to 12 times, depending on the number of dilutions desired. The result is a two-fold serial dilution of test compound in the enrichment broth.

Each vessel is then inoculated with a cell suspension of the appropriate test organism. Bacteria are grown in broth and fungi on agar slants, for a time and at a temperature appropriate to the species being tested. At the end of the growth period, the broth is vortexed to disperse the cells. In the case of fungi, the spores are harvested by pipetting water onto the slant and dislodging the spores with a sterile loop The cell/spore suspensions are standardized by controlling incubation time and temperature and the volume of the diluent. Once inoculated, the vessels are incubated at the appropriate tem- Results From Speed of Kill Test
Active Ingredient = Structure I 3 parts ($R^1$ = ClR = H, Y = $CH_3$) + 1 part (R = $R^1$ = H, Y = $CH_3$)

| Sample # | % AI | Stabilizer | % Stabilizer | Solvent | SOK in synthetic hard water 30 minutes | 4 hr | SOK in Mg9 Medium 30 minutes | 4 hr |
|---|---|---|---|---|---|---|---|---|
| | | | | | | | 5.00 log reduction | |
| 1 | 14 | TEOF | 9 | BCA | 0/8 | >5.00 | 250 ppm | 32 ppm |
| 2 | 14 | TEOF | 9 | BCA | 0/8 | >5.00 | 250 ppm | 32 ppm |
| 3 | 14 | magnesium nitrate | 15 | water | 0/8 | >5.00 | 250 ppm | 32 ppm |
| 4 | 1.5 | TEOF | 2 | DPG | 1/8 | >5.00 | 250 ppm | 32 ppm |
| 5 | 1.5 | magnesium nitrate / copper nitrate | 1.6 / 0.15 | water | 0/8 | >5.00 | 250 ppm | 32 ppm |

EXAMPLE 34

The minimum inhibitory concentration (MIC) of both nitrate stabilized and orthoformate stabilized isothiazolone was determined and found to be equivalent.

perature, and then examined for growth/no growth. The minimum inhibitory concentration (MIC) is defined as the lowest concentration of compound that results in complete inhibition of growth of the test organism.

Minimum Inhibitory Concentration (ppm AI)
Active Ingredient = Structure I 3 parts ($R^1$ = Cl, R = H, Y = $CH_3$) + 1 part ($R^1$ = R = H, Y = $CH_3$)

| Sample | % AI | Stabilizer | % Stabilizer | Solvent | Psfl | Psae | Saur | Ecol | Calb | Anig | Apul |
|---|---|---|---|---|---|---|---|---|---|---|---|
| 1 | 14 | TEOF | 9 | BCA | 2 | 8/4 | 16 | 4 | 1 | 2 | 1 |
| 2 | 14 | TEOF | 9 | BCA | 2 | 4 | 16 | 8 | 2/1 | 2 | 1 |
| 3 | 14 | magnesium nitrate | 15 | water | 2 | 4 | 16 | 8 | 2 | 2 | 1 |
| 4 | 1.5 | TEOF | 2 | DPG | 2 | 8 | 16 | 4 | 2 | 2 | 2 |
| 5 | 1.5 | magnesium nitrate / copper nitrate | 1.6 / 0.15 | water | 2 | 4 | 16 | 4 | 2 | 2 | 2/1 |

Psfl = *Pseudomonas fluorescens*
Psal = *Pseudomonas aeruginosa*
Saur = *Staphylococcus aureus*
Ecol = *Escherichia coli*
Calb = *Candida albicans*
Anig = *Aspergillus niger*
Apul = *Aureobasidium pullulans*

Minimum Inhibitory Concentration Test

A minimum inhibitory concentration (MIC) test is used to evaluate the antimicrobial activity of a test compound in preservative applications. The MIC value is obtained in the following manner. A volume of the stock solution containing 1% AI is dispensed into enrichment broth to give an initial starting test concentration of 250 ppm compound.

At the start of the test, each vessel in the dilution series, except the first vessel, contains an equal volume of the compound free broth. The first vessel contains twice the volume of broth with the starting concentration of test compound. One-half of the broth from the

What is claimed is:
1. A stabilized composition comprising a compound of the formula:

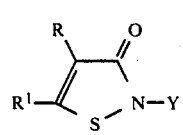

wherein Y is substituted or unsubstituted alkyl, unsubstituted or halo substituted alkenyl or alkynyl, and unsubstituted or substituted cycloalkyl, aralkyl or aryl and R and $R^1$ are hydrogen, halo or alkyl and an effective amount of an orthoester of the formula: C X(OR$^2$)(OR$^3$)(OR$^4$) wherein X is hydrogen, alkyl, OR$^5$ or aryl; $R^2$, $R^3$, $R^4$ and $R^5$ are the same or different radical selected from alkyl, cycloalkyl, aryl, alkylaryl or arylalkyl.

2. The composition of claim 1 which comprises from 0.1 to 99.9 parts of one or more compounds of the

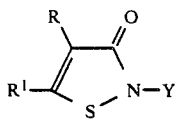

wherein R, $R^1$ and Y are as defined in claim 1 and from 0.1 to 99.9 parts of an orthoester of the formula:

C X(OR$^2$)(OR$^3$)(OR$^4$)

wherein x, $R^2$, $R^3$ and $R^4$ are as defined in claim 1 and from 0 to 99.8% of an organic solvent.

3. The composition of claim 2 which comprises from 1 to 50 parts of the isothiazolone; from 1 to 25 parts of the orthoester and from 25 to 98 parts of a solvent.

4. The composition of claim 3 which comprises from 1 to 25 parts of the isothiazolone, from 1 to 10 parts of the orthoester and from 30 to 98 parts of a solvent.

5. The composition of claim 4 wherein Y is $C_1$-$C_{18}$alkyl or $C_3$-$C_{12}$cycloalkyl; R is hydrogen or halo and $R^1$ is hydrogen or halo and $R^2$, $R^3$, $R^4$ are lower alkyl, and X is hydrogen, alkyl, or aryl.

6. The composition of claim 5 which comprises 14 parts of an isothiazolone selected from 5-chloro-2-methyl-3-isothiazolone, 2-methyl-3-isothiazolone, 2-octyl-3-isothiazolone, or 4,5-dichloro-2-octyl-3isothiazolone.

7. The composition of claim 5 which comprises 1.5 parts of an isothiazolone selected from 5-chloro-2-methyl-3-isothiazolone, 2-methyl-3-isothiazolone, 2-octyl-3-isothiazolone, or 4,5-dichloro-2-octyl-3isothiazolone.

8. The composition of claim 6 which comprises an orthoester selected from trimethyl orthoformate, triethyl orthoformate, triethyl orthoacetate, trimethyl orthovalerate or trimethyl orthobenzoate.

9. A method for stabilizing a compound of the formula

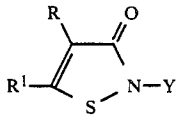

wherein Y is substituted or unsubstituted alkyl, unsubstituted or halo substituted alkenyl, and unsubstituted or substituted cycloalkyl, aralkyl or aryl and R and $R^1$ are hydrogen, halo or alkyl, useful for inhibiting the growth of bacteria, fungi, or algae in a locus subject to contamination by bacteria, fungi, or algae, comprising using in association with said compound an effective stabilizing amount of an orthoester of the formula: CS(OR$^2$)(OR$^3$)(OR$^4$) wherein X is hydrogen, alkyl, OR$^5$ or aryl, $R^2$, $R^3$, $R^4$ and $R^5$ are the same or different radical selected from alkyl, cycloalkyl, aryl, alkylaryl or arylalkyl.

10. The method of claim 9 wherein the weight ratio of said orthoester to said compound is about 1:7 to about 1.5:1.

11. Method of claim 9 wherein said compound is present in the form of a concentrated solution and the weight ratio of orthoester to compound is about 1:4 to about 1:2.

* * * * *

UNITED STATES PATENT AND TRADEMARK OFFICE
CERTIFICATE OF CORRECTION

PATENT NO.   :   4,906,274
DATED        :   March 6, 1990
INVENTOR(S)  :   John R. Mattox It is certified that error appears in the above-identified patent and that said Letters Patent is hereby corrected as shown below:

In claim 9, line 4 after "alkenyl" should be

-- or alkynyl --

In claim 9, line 10 "CS" should be

-- CX --.

Signed and Sealed this

Nineteenth Day of March, 1991

Attest:

HARRY F. MANBECK, JR.

Attesting Officer    Commissioner of Patents and Trademarks